US008853603B2

(12) United States Patent
Sheehan

(10) Patent No.: US 8,853,603 B2
(45) Date of Patent: Oct. 7, 2014

(54) THERMO-FORMABLE SUPPORT PRODUCTS AND HEATING MEANS THEREFOR

(75) Inventor: David Sheehan, Kilmacleague Dunmore East (IE)

(73) Assignee: Fastform Research Ltd. (IE)

( * ) Notice: Subject to any disclaimer, the term of this patent is extended or adjusted under 35 U.S.C. 154(b) by 447 days.

(21) Appl. No.: 12/774,228

(22) Filed: May 5, 2010

(65) Prior Publication Data

US 2011/0114635 A1 May 19, 2011

(30) Foreign Application Priority Data

May 5, 2009 (IE) .................................. S2009/0350

(51) Int. Cl.

| | |
|---|---|
| ***H05B 6/64*** | (2006.01) |
| ***A61F 5/01*** | (2006.01) |
| ***A61F 5/058*** | (2006.01) |
| ***B65D 81/34*** | (2006.01) |

(52) U.S. Cl.

CPC ............... *A61F 5/01* (2013.01); *A61F 5/05825* (2013.01); *B65D 81/3461* (2013.01)

USPC ................................. 219/759; 602/7; 602/14

(58) Field of Classification Search

None

See application file for complete search history.

(56) References Cited

U.S. PATENT DOCUMENTS

| | | | | |
|---|---|---|---|---|
| 4,685,453 | A * | 8/1987 | Guignard et al. | 602/7 |
| 5,093,176 | A | 3/1992 | Pribonic et al. | |
| 5,630,959 | A * | 5/1997 | Owens | 219/730 |
| 7,438,697 | B2 * | 10/2008 | Campagna et al. | 602/8 |
| 2001/0043971 | A1 | 11/2001 | Johns | |
| 2005/0269318 | A1 | 12/2005 | Zafiroglu et al. | |
| 2007/0029314 | A1 | 2/2007 | Rodgers et al. | |
| 2007/0218241 | A1 | 9/2007 | Eckerman | |
| 2008/0154164 | A1 * | 6/2008 | Sheehan et al. | 602/7 |

FOREIGN PATENT DOCUMENTS

| | | | | |
|---|---|---|---|---|
| DE | 3639717 | A1 * | 6/1988 | F24F 6/10 |
| WO | WO-2008/041215 | A1 * | 4/2008 | A61F 5/01 |

* cited by examiner

*Primary Examiner* — Johannes P Mondt

(74) *Attorney, Agent, or Firm* — One3 IP Management, P.C.; Jeromye V. Sartain

(57) ABSTRACT

A packaged product, such as a thermo-formable splinting or bracing product adapted to be heated by microwave energy, which packaged product comprises a water laden absorbent material (5), optionally sealed in a first water-impervious container (6), wherein said absorbent material (5) is adapted to permit microwave energy to enter and heat the water held in the absorbent material (5), the first container (6) being microwave transparent and the product to be heated and the absorbent material are disposed adjacent each other but are separated by a water-impervious barrier.

16 Claims, 1 Drawing Sheet

THERMO-FORMABLE SUPPORT PRODUCTS AND HEATING MEANS THEREFOR

BACKGROUND OF THE INVENTION

Related Applications

This application claims priority and is entitled to the filing date of Irish Patent Appln. No. S2009/0350, filed May 5, 2009, and entitled “Thermo-Formable Support Products and Heating Means Therefor.” The contents of the aforementioned application are incorporated by reference herein.

Incorporation by Reference

Applicant hereby incorporates herein by reference any and all U.S. patents and U.S. patent applications cited or referred to in this application.

Field of the Invention

This invention relates to products and their packaging which can be heated by microwave energy. More particularly, this invention relates to thermoplastic polymeric products used for supporting body portions and to methods for the use thereof. Such products include splints, casts and braces for supporting animal body members, e.g. limbs, the trunk and/or neck of an animal body. Herein such products are thermo-formable and can be heated to skin tolerant temperatures and moulded around the body portion to be treated. Herein these thermo-formable products will be generally referred to as “splints” or “splinting products.”

Splints usually comprise a layer or substrate of a substantially rigid thermoplastic polymeric material such as a polycaprolactone. The polymeric substrate may carry a layer of a padding material on its body facing surface.

In use the splint is heated until it is sufficiently pliable to be wrapped around and conform to the shape of the body portion to be treated. The splint is then allowed to cool and “set.”

Heating of the splint is conventionally carried out by immersion in a hot water bath. However, there are several disadvantages to this method. Firstly, there is the danger of scalding to both the technician and patient from the hot water. Secondly, if the padding material is attached to the polymer substrate, it will become wet and, at the very least, will be uncomfortable to the wearer until it dries out. Since the padding is likely to retain water, the risk of scalding the patient will be further increased. A third disadvantage is that the provision of facilities to house the water bath and its associated heating increases the cost of the treatment and limits the availability of the treatment to fixed locations. The use of water baths additionally increases the likelihood of the splinting product coming into contact with infection hazards such as bacteria, particularly if the water is not frequently renewed.

Attempts to “dry heat” the splint, including the use of conventional microwave apparatus have been largely unsuccessful because it has been difficult to uniformly heat the product safely without creating hotspots which could burn the patient.

Conventionally, microwave ovens used for heating food products operate at a frequency of 2.45 GHz as this is the optimum frequency for exciting the dipolar water molecules contained in the foodstuff, between zero and 100° C. The polymer substrate of a splint will contain little, if any, water and may contain dipolar molecules which have a relative permittivity ($\epsilon$) different from that of water and therefore cannot be heated sufficiently in a microwave oven operating at 2.45 GHz. The geometry of the splint substrate may be very complex, especially if it is at least partially comprised of areas having a web-like conformation and direct heating with microwave energy may cause areas of the splint to overheat due to the well known “Edge Overheating Phenomenon”, thereby resulting in local hotspots and consequential burning of the patient.

SUMMARY OF THE INVENTION

The present invention seeks to provide means for heating thermoplastic polymer splints, including splints bearing a skin-contacting padding layer, safely and uniformly, using heating apparatus which does not suffer from the disadvantages associated with the prior art hot water baths.

According to aspects of the present invention, there is provided a packaged product comprising a product to be heated and a water-laden absorbent material wherein said absorbent material is adapted to permit microwave energy to enter and heat the water held in the water-laden absorbent material; and the product to be heated and the absorbent material are disposed adjacent each other but are separated by a water-impervious, microwave transparent barrier.

An advantage of the present invention described herein is that the transfer of energy to a thermoplastic splint does not rely solely on the principle of heat energy in the form of steam boiling and then condensing on the surface of the object being heated as in the prior art. In fact it is desirable in the present invention that any steam generated remains inside the sealed pouch containing the water-laden absorbent material throughout the heating process. It has been discovered that the presence of an absorbent pad containing water in close proximity to the substrate product to be heated attenuates the microwave irradiation during heating and changes favorably the permittivity values of the nearby thermoplastic splint material and decreases the so called “Edged heating phenomena” common in heating food. This results in more even heating of the substrate product and reduced “hot spots”.

In the absence of the absorbent pad containing water, the applicant found that the substrate being heated suffered severe “hot spots” and began to burn and smell after a short time when exposed to microwave irradiation.

Thus, in accordance with the invention, the absorbent material laden with water, acts as an attenuator and regulates the microwaves favourably to prevent burning. Thus more even heat distribution is achieved throughout the product to be heated, thereby avoiding “hot spots”. In addition to this, cold spots are avoided through the parallel effect of heat being transferred through the barrier or pouch containing the absorbent material in those affected areas.

The usefulness of using the packaged product of the invention to heat substrates such as thermoplastic splints is that the substrate product can be conveniently heated easily, safely, and quickly in a microwave oven, which is a familiar mode of heating for many people in developed countries.

Characterizing features of the invention are set forth in the appended claims.

In one aspect, the product to be heated may comprise a thermo-formable polymeric body supporting product or body member supporting product while in another aspect, the product to be heated may comprise a foodstuff.

Thus, the present invention, in one aspect, provides a packaged product comprising a product to be heated, in combination with a water laden absorbent material, wherein said absorbent material is adapted to permit microwave energy to enter and heat the water held in the water-laden absorbent material, and the product and the absorbent material are disposed adjacent each other but are separated by a water-impervious, microwave transparent barrier.

The water-laden absorbent material may be sealed in a first water-impervious, microwave transparent container.

In one embodiment, the invention provides a packaged product comprising a thermo-formable splint in combination with a water laden absorbent material sealed in a water-impervious, microwave transparent container wherein said absorbent material is adapted to permit microwave energy to enter and heat the water held in the water-laden absorbent material, and the splint and the absorbent material are disposed adjacent each other but are separated by a water-impervious, microwave transparent barrier.

The water laden absorbent material may be sealed in a second water-impervious microwave transparent container, particularly, in the form of a pouch.

As used herein, the water laden absorbent material either alone or sealed in a first or second container will be referred to as a "heater pad".

Throughout this specification, the terms "microwave transparent" and "microwave energy transparent" mean "unreactive to microwave energy". Materials which are microwave transparent (i.e. unreactive to microwave energy) are characterized by having a structure which lacks dipolar molecules. Suitably, the microwave transparent barrier, container or pouch material may comprise a polyethylene. Thus, the microwave transparent barrier, container or pouch may be produced from "Food Grade" polyethylene.

BRIEF DESCRIPTION OF THE DRAWINGS

Although the present invention may be used to heat many products, including foodstuffs, it is particularly useful for thermo-formable splints and is described and illustrated with particular reference to such products by way of example.

In the drawings.

DETAILED DESCRIPTION

The thermoplastic polymers employed in the present invention should be reactive to microwave energy, i.e., should contain dipolar molecules. Polymers which are useful in the present invention include those based on the caprolactone molecule. The polymeric splint material may comprise homopolymers of caprolactone or polymer blends thereof, either alone or in admixture with fillers such as fibrous ligneous materials. Preferred splinting products for use in the present invention are those described in the applicant's published patent specifications Nos. US20080154164 and WO20080412151, the disclosures of which are incorporated herein by reference and inter alia disclose a thermo-formable polymeric body supporting product comprising a member formed from a composite material including a polycaprolactone and a ligno-cellulose additive, said composite material being formable at a forming temperature above ambient temperature and being substantially rigid at ambient temperature and wherein the member has one or more openings through at least part thereof disposed such that the flexural strength of the member in a first direction is greater than that in a second direction.

It will be appreciated by those skilled in the art that the exact configuration of the packaged product may take a number of forms to suit particular applications without departing from the spirit and scope of the present invention. Accordingly, it will be further appreciated that the configuration of the apparatus shown and described and the particular materials of construction are exemplary and that the invention is not so limited, but instead may involve, for example, other materials now known or later developed suitable to the context.

The most preferred splinting products are multi-component products comprising a thermoplastic polymer substrate bearing a skin-contacting padding layer over one surface of the substrate. Such multi-component splinting products are disclosed in the applicant's aforementioned published patent specifications.

Figure 1:
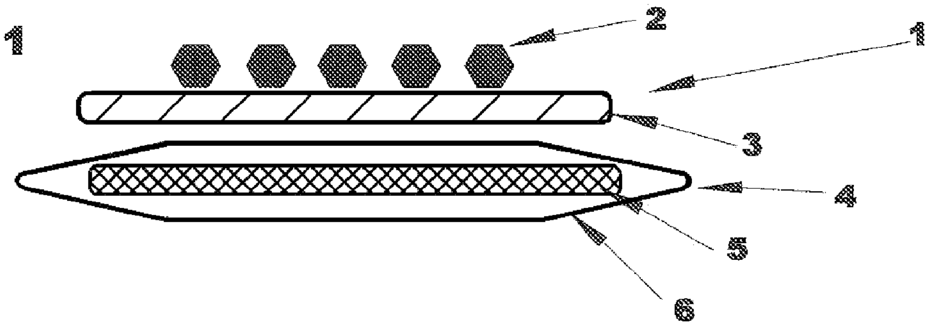
FIG. 1 schematically illustrates the general arrangement of the components of the products according to aspects of the invention in one embodiment.

Referring to FIG. 1, the thermo-formable splint (also referred to herein as a splinting product) (1) comprises the thermoplastic substrate (2) bonded to a skin-contact layer (3) which may aptly be a spacer fabric material. The splint (1) is disposed immediately adjacent the heater pad (4) which comprises a water laden absorbent material (5) sealed in a water-impervious, microwave transparent, aptly, heat-conducting pouch (6).

Figure 2:
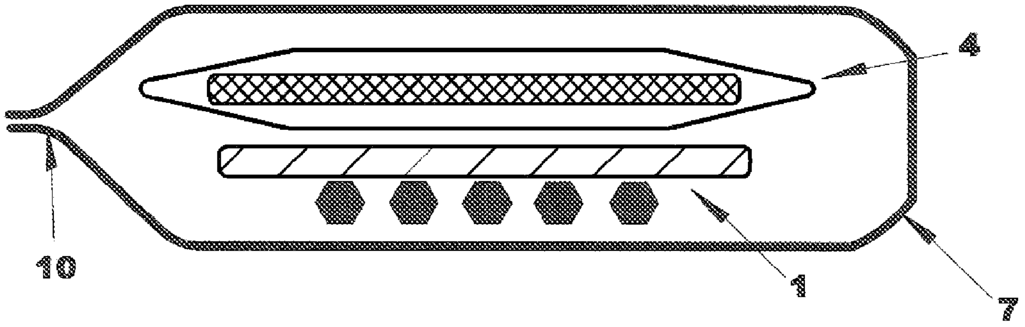
FIGS. 2, 3 and 4 schematically illustrate further aspects of the invention according to a number of embodiments having variations of particular dispositions of the product, heater pad and packaging.

Aptly, as shown in FIG. 2, the splint (1) and the heater pad (4) are packaged within an outer container (7) formed from a water-impervious, microwave energy transparent material. The outer container (7) may be of rigid construction or, more preferably, is in the form of a flexible pouch.

Thus, according to aspects of this embodiment of the invention, the splint (1) and heater pad (4) are contained in a single outer container (7).

Figure 3:
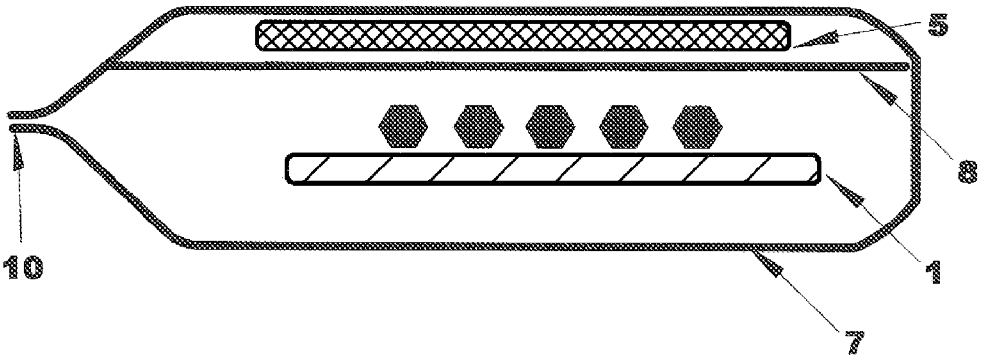
Figure 4:
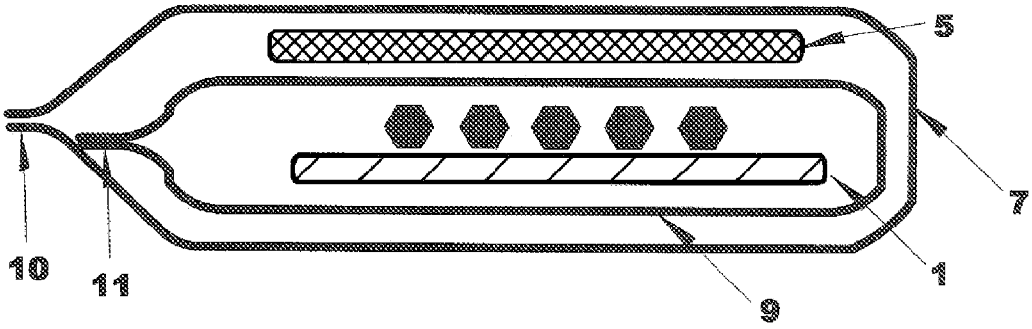

Alternatively, as shown in FIGS. 3 and 4, the splint (1) and water laden absorbent material (5) may be contained in separate compartments or pouches. Preferably, a vacuum is created in each compartment or pouch to ensure better contact and heat transmission.

Thus, as shown in FIG. 3, pouch 7 is provided having two compartments, separated by a water-impervious, microwave transparent membrane or septum (8), wherein the first compartment contains said water laden absorbent material (5) and the second compartment contains the splinting product (1).

In the embodiment shown in FIG. 4, the splint (splinting product) (1) is contained in a separate inner pouch (9) of a water-impervious, microwave transparent material. The heater pad or water laden absorbent material (5) together with the splint (1) contained in the inner pouch (9) are further enclosed in the outer pouch (7). Preferably, the splint (1) is vacuum sealed within the inner pouch (9). The pouches that contain the splints are preferably made from a laminate of Polyethylene and Nylon so as to ensure a vacuum is maintained in the package for a long period of time, for example at least 1 year. More preferably, the inner pouches (9) are weld-sealed and made from 30μ Nylon/50μ Low Density Polyethylene (LDPE) laminate.

The compartments or pouches may also be provided with pressure relieving means (10, 11). For example, a frangible rupture seal (10) may be provided for the pouch which contains only the water laden absorbent material (5) in order to vent excess steam build-up within the package and prevent distortion or contamination of the splinting product (1). Pressure relieving means (11) may be provided for the pouch or compartment containing the splinting product (1) to allow the atmosphere within the pouch or compartment to be reduced, causing deformation of the pouch or compartment walls and allowing the splinting product (1) and absorbent material (5) to be more closely adjacent.

The compartments or pouches which contain the splint (1) are also provided with means to allow ready removal of the heated splint. The removal means and the pressure releasing, whilst independently operable, may be formed into a unitary device.

The splint (1) and heater pad (4;5) should be arranged to lie adjacent each other as closely as possible whether both components are packaged together or placed separately in the microwave heater. We have found that the presence of the heater pad (4;5) in close proximity to the product to be heated, (for example, where the product comprises a thermoplastic splint) will cause the microwave irradiation to be attenuated during heating. This effectively favourably changes the permittivity values of the adjacent product and decreases the so called "edge heating phenomena" a problem commonly found in heating food. The geometry of thermoplastic splints (1) is complex. For example, splints and braces such as those described in the aforesaid patent publications Nos. US20080154164 and WO20080412151 have areas in the form of open webs and other areas configured as rib-like protuberances. The non-uniformity of overall shape or cross-sectional area and variances in microwave radiation distribution patterns in microwave ovens alters the permittivity of the product material in differing places. Thus, when heated directly, energy is absorbed faster in certain areas particularly where over abundant microwave radiation exists, and thus starts to melt the polymer prematurely in these areas while other areas are slower to heat. The polymer molecules in those areas start to oscillate at a higher frequency (compared to the frequency of oscillation when the polymer is in the solid state) and the temperature in these local areas increases dramatically, causing hot spots. Other areas of the product material may exhibit cool spots. A water laden absorbent material (5) adjacent but not touching the product to be heated, attenuates the microwave irradiation during heating and changes favourably the permittivity values of the adjacent product thereby improving heat distribution across the area of the adjacent product being heated, resulting in a more uniform heat distribution and a reduced tendency for hot and cool spots to occur.

The edge heating phenomena may be further attenuated if the heater pad (4;5) is placed in close proximity to the skin-contacting padding layer of a multi-component splinting product (1). The even distribution of heat will reduce the occurrence of hot spots and enable higher microwave energy settings to be used and/or shorten time for heating. Even distribution of heat also prevents the occurrence of "cool spots" since evaporated water contacting and condensing on the areas of the pouch material (6, 7, 9 or septum (8) adjacent any cooler spots on the polymer substrate of the splint will heat such areas.

The water absorbent material (5) may comprise any known material which will absorb and retain water. Such materials may comprise a hydrogel such those based on celluloses or be composed, at least in part, of hydrophilic fibres such as those known as super absorbing polyolefin filaments. Preferably, the water absorbent material (5) comprises a non-woven fabric of acrylic polymer fibres or filaments. The water absorbent material (5) comprises a material which permits microwave heating of the absorbed water held in the water absorbent material (5).

Preferably, the water absorbent material (5) contains and retains sufficient absorbed water such that no free water exists outside the water absorbent material (5). Therefore, the water loading of the absorbent material is not more than the amount to just saturate the material. This ensures even distribution of water over the cross sectional area of the product (1) being heated by microwave energy and therefore ensures more even heat absorption and dissipation into the underlying substrate. Aptly, the absorbent material contains water in an amount ranging from 0.01 to 0.15 ml.cm$^2$. Typically, the absorbent material (5) will contain about 0.05 ml of water per cm$^2$ of absorbent material.

The water laden absorbent material (5) may lie adjacent the body-contacting padding material (3) which may form part of the splint (1) in order to ensure not only adequate and even heating of the thermo-formable polymer (2) but also to control the amount of heat applied to the body-contacting padding layer (3) of the splint (1). Since the permittivity of the padding (3) will be different from that of the polymer substrate (2) the body-contacting padding layer (3) is not heated to the same temperature as that of the substrate (2).

Depending on the power of the microwave energy employed and other characteristics of the energy source, the time setting should be calibrated to allow heating of the thermoplastic substrate (2) to a temperature such that it becomes sufficiently pliable to be wrapped or formed around the body portion to be supported and yet not high enough to cause discomfort or burning of the skin. For a domestic microwave oven generating energy at a frequency of 2.54 GHz we have found, for example, a time of a about 3 minutes is required to heat the polymer substrate (2) of a lower arm splint to about 60° C.

The invention will now be illustrated by way of example only with reference to the following Example. Again, those skilled in the art will appreciate that the Example is merely illustrative of aspects of the present invention and not limiting thereof.

EXAMPLE

A heater pad was formed by inserting 50 ml of water into a 125 micron PE pouch containing an absorbent pad measuring 300 mm×330 mm and the pouch was sealed, using a heat sealer. The absorbent pad was made from a commercial grade of Biocomponent Polyolefin Superabsorbent Fibres.

The heater pad was placed inside a commercial microwave oven (Sharp model R21AT), rated at 1000 watts at 100% power setting and a thermoplastic substrate (e.g. a blank for a lower arm splint), roughly having the same dimensions as the heater pad was placed on top of the heater pad.

The power of the oven was adjusted to the 60% setting (equating to 600 watts) and switched on for 3 minutes.

After 3 minutes the thermoplastic splint was removed and was found to be fully activated. The product was soft and pliable and there was no evidence of over-heating, hot spots, burning or smell.

Packaged products of the invention will include any product or material to be heated up to temperatures generally within the boiling range of the water contained in the water absorbing material. Such products or materials to be heated may include foodstuffs and thermoplastic materials in addition to thermo-formable splints.

The packaged products of the invention are ideally suited for microwave heating but they may be heated in conventional water baths since they are kept separated from the heating environment.

It will of course be understood that the present invention is not limited to the details herein described and that such are given by way of example only. Rather, the scope of the invention is to be interpreted only in conjunction with the appended claims and it is made clear, here, that the inventor(s) believe that the claimed subject matter is the invention.

What is claimed is:

1. A packaged product comprising:

a sealable water-impervious, microwave transparent container containing a water-laden absorbent material, wherein the absorbent material is sealed in the water-impervious, microwave transparent container and is configured to permit microwave energy to enter and heat the water held in the water-laden absorbent material; and a thermo-formable polymeric body or body member supporting product to be heated, wherein the product to be heated and the absorbent material are disposed adjacent but not touching each other and are separated from each other by the water-impervious, microwave transparent container.

2. The packaged product of claim 1 wherein the product to be heated comprises a layer of skin-contacting padding material.

3. The packaged product of claim 2, wherein the padding layer is disposed to lie adjacent the absorbent material.

4. The packaged product of claim 1 wherein the water absorbent material contains and retains sufficient absorbed water such that no free water exists outside the water absorbent material.

5. The packaged product as claimed of claim 1 wherein the container is provided with a frangible rupture seal.

6. The packaged product of claim 1 wherein the water absorbent material is selected from the group comprising: hydrogels and hydrophilic polymer fibres or filaments.

7. The packaged product of claim 1 wherein the thermo-formable polymeric body or body member supporting product comprises a member formed from a composite material including a polycaprolactone and a ligno-cellulose additive, the composite material being formable at a forming temperature above ambient temperature and being substantially rigid at ambient temperature and wherein the member has one or more openings through at least part thereof disposed such that the flexural strength of the member in a first direction is greater than that in a second direction.

8. The packaged product of claim 1, wherein:

the water-impervious microwave transparent container and the product to be heated are wholly enclosed by a second water-impervious, microwave transparent container.

9. The packaged product of claim 1, wherein:

a septum is formed within the sealable water-impervious microwave transparent container, said septum separating the product to be heated from the water-laden absorbent material.

10. The packaged product of claim 1, wherein:

the product to be heated is contained in a second container that is wholly enclosed by said sealable water-impervious, microwave transparent container, wherein said second container is sealable, water-impervious and microwave transparent.

11. A packaged product comprising:

a sealable first water-impervious, microwave transparent container containing a water-laden absorbent material, wherein the absorbent material is sealed in the first water-impervious, microwave transparent container and is configured to permit microwave energy to enter and heat the water held in the water-laden absorbent material; and a thermo-formable polymeric body or body member supporting product to be heated enclosed in a second water-impervious, microwave transparent container to separating the product to be heated from the absorbent material.

12. The packaged product of claim 11 wherein the product to be heated and the absorbent material are sealed in the first water-impervious microwave transparent container.

13. The packaged product as claimed of claim 11 wherein the second container is wholly enclosed by the first container.

14. The packaged product as claimed in of claim 8 wherein the first container is separated by a septum into two compartments, one of the compartments defining the second container.

15. The packaged product of claim 11 wherein the second container is provided with a frangible rupture seal capable of relieving gas pressure in said second container.

16. A packaged product comprising a product to be heated to a temperature up to the boiling temperature of water, in combination with a sealable first water-impervious, microwave transparent container containing a water-laden absorbent material, wherein:

the absorbent material is sealed in the first water-impervious, microwave transparent container and is configured to permit microwave energy to enter and heat the water held in the absorbent material;

the product to be heated is a thermo-formable polymeric body or body member supporting product; and the product and the absorbent material are disposed adjacent but not touching each other and are separated by the first water-impervious, microwave transparent container.

* * * * *